United States Patent
Maeno et al.

(10) Patent No.: US 11,523,592 B2
(45) Date of Patent: *Dec. 13, 2022

(54) PEARL CULTURE MATERIAL, NUCLEUS INSERTION METHOD, AND PEARL CULTURE MATERIAL COMPOSITION

(71) Applicant: FUJIFILM CORPORATION, Tokyo (JP)

(72) Inventors: Yutaka Maeno, Kanagawa (JP); Kazutaka Chibana, Kanagawa (JP); Hidehiro Mochizuki, Kanagawa (JP); Tadanori Yamada, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/225,127

(22) Filed: Apr. 8, 2021

(65) Prior Publication Data

US 2021/0227802 A1    Jul. 29, 2021

Related U.S. Application Data

(63) Continuation of application No. PCT/JP2019/039666, filed on Oct. 8, 2019.

(30) Foreign Application Priority Data

Oct. 12, 2018  (JP) .............................. JP2018-193668

(51) Int. Cl.
| | | |
|---|---|---|
| A01K 61/54 | (2017.01) | |
| A01K 61/57 | (2017.01) | |
| C07K 14/325 | (2006.01) | |
| C07K 14/78 | (2006.01) | |

(52) U.S. Cl.
CPC .............. *A01K 61/54* (2017.01); *A01K 61/57* (2017.01); *C07K 14/325* (2013.01); *C07K 14/78* (2013.01)

(58) Field of Classification Search
None
See application file for complete search history.

(56) References Cited

U.S. PATENT DOCUMENTS

| | | | | |
|---|---|---|---|---|
| 6,514,614 B1* | 2/2003 | Komatsu | ................ | A01K 61/54 428/407 |
| 8,349,589 B2* | 1/2013 | De Boer | ................ | A61P 35/00 435/69.1 |
| 8,481,493 B2* | 7/2013 | Lurvink | ................ | A61L 27/24 514/17.2 |
| 9,157,078 B2* | 10/2015 | Ogiwara | ................ | C12N 11/02 |
| 2017/0304458 A1 | 10/2017 | Van Spreuwel-Gooss | | |
| 2019/0144525 A1* | 5/2019 | Muraya | ................ | C12N 5/0018 435/69.1 |
| 2020/0296940 A1* | 9/2020 | Amao | ................ | A01K 61/56 |

FOREIGN PATENT DOCUMENTS

| | | |
|---|---|---|
| CN | 1294845 A | 5/2001 |
| CN | 101356901 A | 2/2009 |
| CN | 101366364 B | 11/2010 |
| CN | 101991588 A | 3/2011 |
| CN | 103210855 A | 7/2013 |
| CN | 105265353 A | 1/2016 |
| CN | 105284674 A | 2/2016 |
| CN | 105309341 A | 2/2016 |
| CN | 105309345 A | 2/2016 |
| CN | 105309346 A | 2/2016 |
| CN | 105309347 A | 2/2016 |
| CN | 105475183 A | 4/2016 |
| CN | 107073165 A | 8/2017 |
| EP | 2112997 B1 | 8/2012 |
| JP | H01-148135 A | 6/1989 |
| JP | H02-203724 A | 8/1990 |
| JP | H03-87128 A | 4/1991 |
| JP | H05-236848 A | 9/1993 |
| JP | H07-132032 A | 5/1995 |
| JP | H11-56161 A | 3/1999 |
| JP | 2003-105183 A | 4/2003 |
| JP | 2006-296274 A | 11/2006 |
| JP | 2006-304628 A | 11/2006 |
| WO | 2015/033972 A1 | 3/2015 |
| WO | 2016/063935 A1 | 4/2016 |
| WO | 2019/087650 A1 | 5/2019 |

OTHER PUBLICATIONS

English translation PDF of JP-H05-236848 (A) Description section Published Sep. 17, 1993 (Year: 1993).*
English translation PDF of JP-H05-236848 (A) Abstract section Published Sep. 17, 1993 (Year: 1993).*
English language translation of the following: Office action dated Jul. 28, 2021 from the SIPO in a Chinese patent application No. 201980067304.0 corresponding to the instant patent application. This office action translation is submitted now in order to supplement the understanding of the cited references which are being disclosed in the instant Information Disclosure Statement.
International Search Report issued in International Application No. PCT/JP2019/039666 dated Dec. 17, 2019.
Written Opinion of the ISA issued in International Application No. PCT/JP2019/039666 dated Dec. 17, 2019.

(Continued)

*Primary Examiner* — Anand U Desai

(74) *Attorney, Agent, or Firm* — Solaris Intellectual Property Group, PLLC

(57) ABSTRACT

There are provided a pearl culture material containing at least one selected from the group consisting of a pearl nucleus and a mantle, and the at least one selected from the group consisting of a pearl nucleus and a mantle contains a protein having 10 EU/g or less of an endotoxin amount, a nucleus insertion method, and a pearl culture material composition.

9 Claims, No Drawings

Specification includes a Sequence Listing.

(56) References Cited

OTHER PUBLICATIONS

Jinfen Wei et al., "Differentially expressed immune-related genes in hemocytes of the pearl oyster *Pinctada fucata* against allograft identified by transcriptome analysis", Fish & Shellfish Immunology, Academic Press, London, GB, vol. 62, p. 247-256, Jan. 2017.
Claudia Rabert et al., "Recombinants proteins for industrial uses: utilization of Pichia pastoris expression system", Brazilian Journal of Microbiology, vol. 44, No. 2, p. 351-356, Jan. 2013.
Extended European Search Report dated Nov. 18, 2021, issued in corresponding EP Patent Application No. 19870497.5.
English language translation of the following: Office action dated Dec. 27, 2021 from the SIPO in a Chinese patent application No. 201980067304.0 corresponding to the instant patent application. This office action translation is submitted now in order to supplement the understanding of the cited reference which is being disclosed in the instant Information Disclosure Statement.
English language translation of the following: Examiner's Decision of Refusal dated May 12, 2022 from the SIPO in a Chinese patent application No. 201980067304.0 corresponding to the instant patent application.
Anonymous: "Setting new standards for gelatin in-body applications", May 25, 2018, pp. 1-6, Retrieved from the Internet: URL: http://www.manufacturingchemist.com/news/article_page/Setting_new_standards_for_gelatin_in-body_applications/143094.
Office Action dated Aug. 22, 2022, issued by the EPO in corresponding EP Patent Application No. 19870497.5.

\* cited by examiner

SEQUENCE LISTING

```
<160> NUMBER OF SEQ ID NOS: 2

<210> SEQ ID NO 1
<211> LENGTH: 571
<212> TYPE: PRT
<213> ORGANISM: Artificial
<220> FEATURE:
<223> OTHER INFORMATION: Artificial polypeptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125
```

```
Arg Gly Leu Ala Gly Pro Ile Gly Pro Pro Gly Ala Gly Ala Pro
130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                165                 170                 175
Asp Gly Ala Pro Gly Lys Asp Gly Val Arg Gly Leu Ala Gly Pro Pro
                180                 185                 190
Gly Ala Pro Gly Leu Gln Gly Ala Pro Gly Leu Gln Gly Met Pro Gly
                195                 200                 205
Glu Arg Gly Ala Ala Gly Leu Pro Gly Pro Lys Gly Glu Arg Gly Asp
210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Ala Gly Pro Lys Gly Ala Asp Gly Ala Pro Gly Lys
                260                 265                 270
Asp Gly Val Arg Gly Leu Ala Gly Pro Ile Gly Pro Pro Gly Glu Arg
                275                 280                 285
Gly Ala Ala Gly Leu Pro Gly Pro Lys Gly Glu Arg Gly Asp Ala Gly
                290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
                340                 345                 350
Pro Lys Gly Glu Arg Gly Asp Ala Gly Pro Lys Gly Ala Asp Gly Ala
                355                 360                 365
Pro Gly Lys Asp Gly Val Arg Gly Leu Ala Gly Pro Pro Gly Ala Pro
370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
                420                 425                 430
Gly Glu Arg Gly Ala Ala Gly Leu Pro Gly Pro Lys Gly Glu Arg Gly
                435                 440                 445
Asp Ala Gly Pro Lys Gly Ala Asp Gly Ala Pro Gly Lys Asp Gly Val
450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
                500                 505                 510
Ile Gly Pro Pro Gly Pro Ala Gly Ala Pro Gly Ala Pro Gly Leu Gln
                515                 520                 525
Gly Met Pro Gly Glu Arg Gly Ala Ala Gly Leu Pro Gly Pro Lys Gly
                530                 535                 540
```

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
            565                 570

<210> SEQ ID NO 2
<211> LENGTH: 1464
<212> TYPE: PRT
<213> ORGANISM: Homo sapiens

<400> SEQUENCE: 2

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
            35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

-continued

```
Gly Glu Ala Gly Pro Gln Gly Pro Arg Gly Ser Gly Pro Gln Gly
            355                 360                 365
Val Arg Gly Glu Pro Gly Pro Pro Gly Pro Ala Gly Ala Ala Gly Pro
    370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Gly Pro Pro Gly Pro Lys Gly Asn
            420                 425                 430
Ser Gly Glu Pro Gly Ala Pro Gly Ser Lys Gly Asp Thr Gly Ala Lys
        435                 440                 445
Gly Glu Pro Gly Pro Val Gly Val Gln Gly Pro Pro Gly Pro Ala Gly
        450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
            500                 505                 510
Ser Pro Gly Pro Ala Gly Pro Lys Gly Ser Pro Gly Glu Ala Gly Arg
            515                 520                 525
Pro Gly Glu Ala Gly Leu Pro Gly Ala Lys Gly Leu Thr Gly Ser Pro
        530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
            580                 585                 590
Gly Lys Ala Gly Glu Arg Gly Val Pro Gly Pro Pro Gly Ala Val Gly
        595                 600                 605
Pro Ala Gly Lys Asp Gly Glu Ala Gly Ala Gln Gly Pro Pro Gly Pro
        610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
            675                 680                 685
Gly Pro Pro Gly Pro Ala Gly Pro Arg Gly Ala Asn Gly Ala Pro Gly
        690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
            740                 745                 750
Ala Asp Gly Ser Pro Gly Lys Asp Gly Val Arg Gly Leu Thr Gly Pro
            755                 760                 765
```

-continued

Ile Gly Pro Pro Gly Pro Ala Gly Ala Pro Gly Asp Lys Gly Glu Ser
770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Gly Pro Ala Gly Phe Ala Gly Pro
                805                 810                 815

Pro Gly Ala Asp Gly Gln Pro Gly Ala Lys Gly Glu Pro Gly Asp Ala
                820                 825                 830

Gly Ala Lys Gly Asp Ala Gly Pro Pro Gly Pro Ala Gly Pro Ala Gly
                835                 840                 845

Pro Pro Gly Pro Ile Gly Asn Val Gly Ala Pro Gly Ala Lys Gly Ala
850                 855                 860

Arg Gly Ser Ala Gly Pro Pro Gly Ala Thr Gly Phe Pro Gly Ala Ala
865                 870                 875                 880

Gly Arg Val Gly Pro Pro Gly Ser Gly Asn Ala Gly Pro Pro Gly
                885                 890                 895

Pro Pro Gly Pro Ala Gly Lys Glu Gly Lys Gly Pro Arg Gly Glu
                900                 905                 910

Thr Gly Pro Ala Gly Arg Pro Gly Glu Val Gly Pro Pro Gly Pro Pro
                915                 920                 925

Gly Pro Ala Gly Glu Lys Gly Ser Pro Gly Ala Asp Gly Pro Ala Gly
930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
                980                 985                 990

Glu Arg Gly Pro Pro Gly Pro Met Gly Pro Pro Gly Leu Ala Gly Pro
                995                 1000                1005

Pro Gly Glu Ser Gly Arg Glu Gly Ala Pro Gly Ala Glu Gly Ser
                1010                1015                1020

Pro Gly Arg Asp Gly Ser Pro Gly Ala Lys Gly Asp Arg Gly Glu
                1025                1030                1035

Thr Gly Pro Ala Gly Pro Pro Gly Ala Pro Gly Ala Pro Gly Ala
                1040                1045                1050

Pro Gly Pro Val Gly Pro Ala Gly Lys Ser Gly Asp Arg Gly Glu
                1055                1060                1065

Thr Gly Pro Ala Gly Pro Thr Gly Pro Val Gly Pro Val Gly Ala
                1070                1075                1080

Arg Gly Pro Ala Gly Pro Gln Gly Pro Arg Gly Asp Lys Gly Glu
                1085                1090                1095

Thr Gly Glu Gln Gly Asp Arg Gly Ile Lys Gly His Arg Gly Phe
                1100                1105                1110

Ser Gly Leu Gln Gly Pro Pro Gly Pro Pro Gly Ser Pro Gly Glu
                1115                1120                1125

Gln Gly Pro Ser Gly Ala Ser Gly Pro Ala Gly Pro Arg Gly Pro
                1130                1135                1140

Pro Gly Ser Ala Gly Ala Pro Gly Lys Asp Gly Leu Asn Gly Leu
                1145                1150                1155

Pro Gly Pro Ile Gly Pro Pro Gly Pro Arg Gly Arg Thr Gly Asp
                1160                1165                1170

Ala Gly Pro Val Gly Pro Pro Gly Pro Pro Gly Pro Pro Gly Pro

-continued

```
                1175                1180                1185
Pro Gly Pro Pro Ser Ala Gly Phe Asp Phe Ser Phe Leu Pro Gln
        1190                1195                1200
Pro Pro Gln Glu Lys Ala His Asp Gly Gly Arg Tyr Tyr Arg Ala
        1205                1210                1215
Asp Asp Ala Asn Val Val Arg Asp Arg Asp Leu Glu Val Asp Thr
        1220                1225                1230
Thr Leu Lys Ser Leu Ser Gln Gln Ile Glu Asn Ile Arg Ser Pro
        1235                1240                1245
Glu Gly Ser Arg Lys Asn Pro Ala Arg Thr Cys Arg Asp Leu Lys
        1250                1255                1260
Met Cys His Ser Asp Trp Lys Ser Gly Glu Tyr Trp Ile Asp Pro
        1265                1270                1275
Asn Gln Gly Cys Asn Leu Asp Ala Ile Lys Val Phe Cys Asn Met
        1280                1285                1290
Glu Thr Gly Glu Thr Cys Val Tyr Pro Thr Gln Pro Ser Val Ala
        1295                1300                1305
Gln Lys Asn Trp Tyr Ile Ser Lys Asn Pro Lys Asp Lys Arg His
        1310                1315                1320
Val Trp Phe Gly Glu Ser Met Thr Asp Gly Phe Gln Phe Glu Tyr
        1325                1330                1335
Gly Gly Gln Gly Ser Asp Pro Ala Asp Val Ala Ile Gln Leu Thr
        1340                1345                1350
Phe Leu Arg Leu Met Ser Thr Glu Ala Ser Gln Asn Ile Thr Tyr
        1355                1360                1365
His Cys Lys Asn Ser Val Ala Tyr Met Asp Gln Gln Thr Gly Asn
        1370                1375                1380
Leu Lys Lys Ala Leu Leu Leu Gln Gly Ser Asn Glu Ile Glu Ile
        1385                1390                1395
Arg Ala Glu Gly Asn Ser Arg Phe Thr Tyr Ser Val Thr Val Asp
        1400                1405                1410
Gly Cys Thr Ser His Thr Gly Ala Trp Gly Lys Thr Val Ile Glu
        1415                1420                1425
Tyr Lys Thr Thr Lys Thr Ser Arg Leu Pro Ile Ile Asp Val Ala
        1430                1435                1440
Pro Leu Asp Val Gly Ala Pro Asp Gln Glu Phe Gly Phe Asp Val
        1445                1450                1455
Gly Pro Val Cys Phe Leu
        1460
```

PEARL CULTURE MATERIAL, NUCLEUS INSERTION METHOD, AND PEARL CULTURE MATERIAL COMPOSITION

CROSS-REFERENCE TO RELATED APPLICATIONS

This application is a continuation application of International Application No. PCT/JP2019/039666, filed Oct. 8, 2019, the disclosure of which is incorporated herein by reference in its entirety. Further, this application claims priority from Japanese Patent Application No. 2018-193668, filed Oct. 12, 2018, the disclosure of which is incorporated herein by reference in its entirety.

BACKGROUND OF THE INVENTION

1. Field of the Invention

The present disclosure relates to a pearl culture material, a nucleus insertion method, and a pearl culture material composition.

2. Description of the Related Art

A cultured pearl can be produced by inserting a tissue piece of a mantle (hereinafter, also may be referred to as a "mantle piece") and a pearl nucleus into the body of a mother pearl oyster capable of producing a pearl (hereinafter, also may be referred to as "nucleus insertion") and causing a pearl sag to be formed, where the pearl sag causes a nacreous substance to be secreted on the surface of the pearl nucleus, so that a pearl layer is formed on the surface of the pearl nucleus.

In particular, the nucleus insertion is said to be an important process that affects the mortality of the mother pearl oyster and the quality of the pearl (the presence or absence of stains or scratches), which depend on the quality of the nucleus insertion, since the biological defense reaction caused by a foreign matter becomes a heavy burden on the mother pearl oyster in a case where a nucleus obtained by cutting a shell of other species into a spherical shape is inserted into the body of the mother pearl oyster.

For the purpose of improving the compatibility between the living body of the mother pearl oyster and the nucleus, which is a foreign matter, and improving the survival rate of the shellfish and the rate of the high-quality pearl, nuclei coated with various biomaterials such as a peptide, fibronectin, chitosan, and a polylactic acid are disclosed.

For example, there has been disclosed a nucleus for pearl culture, characterized by having, on the surface of a nucleus, a coating film of a mixture of one or two or more selected from the group consisting of collagen, gelatin, and chemical derivatives thereof, where the coating film has a thickness of 0.005 μm or more (see, for example, JP1990-203724A (JP-H02-203724A)).

In addition, there has been disclosed a nucleus for pearl culture, characterized in that the surface of a nucleus for culture is coated with a cell-scaffolding organic substance (for example, fibronectin, fetuin) that is nontoxic to a pearl oyster and is less rejective than a calcium crystal (see, for example, JP1989-148135A (JP-H01-148135A)).

In addition, as a cell activator for pearl culture which is used for treating a cut piece of a mantle of a mother pearl oyster for pearl culture, there has been disclosed a mantle cell activator for pearl culture, characterized by containing an artificial polypeptide which has an Arg-Gly-Asp sequence in the molecule thereof and has a cell adhesion activity and a cell activation activity (see, for example, JP1993-236848A (JP-H05-236848A)).

In addition, there has been disclosed a pearl nucleus characterized in that the surface the nucleus has a positive charge (see, for example, WO2015/033972A).

Various techniques have been proposed for the purpose of obtaining a high-quality pearl having fewer stains or scratches on the surface of the obtained pearl.

For example, as a culture method that makes it possible to secure high-quality mantle pieces and further enhance the quality of a cultured pearl, there has been disclosed a method of culturing a pearl, in which a mantle piece obtained from the mantle of a piece shellfish and a pearl nucleus are transplanted into a mother pearl oyster to culture a pearl, which is characterized by separating epithelial cells from an epithelial tissue of the mantle as the mantle piece, and using the separated epithelial cells after being artificially cultured in vitro (see, for example, JP2006-304628A).

As a nucleus for pearl culture, which is harmless to the mother pearl oyster, is less rejective, and can greatly improve the yield, there has been disclosed a nucleus for pearl culture, which is a nucleus that is inserted into a mother pearl oyster for pearl culture and is characterized in that the nucleus is a molded nucleus obtained by finely crushing a wasted shell of a mother pearl oyster for pearl culture, and sintering and molding the crushed shell (see, for example, JP2006-296274A).

As a method of producing a cultured pearl, in which is shellfishes for pearl culture are trained to be mother pearl oysters, a pearl nucleus is inserted thereto and cultured, and then the generated cultured pearl is taken out, there has been disclosed a method of producing a cultured pearl, which is characterized by inserting a nucleus having a density lower than that of the pearl nucleus after training the mother pearl oyster and before inserting the pearl nucleus, and extracting the nucleus having a density lower than that of the pearl nucleus after a predetermined period of culture (for example, JP1999-056161A (JP-H12-056161A)).

SUMMARY OF THE INVENTION

However, the techniques described in JP1990-203724A (JP-H02-203724A), JP1989-148135A (JP-H01-148135A), JP2006-304628A, WO2015/033972A, JP1993-236848A (JP-H05-236848A), JP1993-236848A (JP-H05-236848A), and JP1999-056161A (JP-H12-056161A) cannot be said to have a sufficiently high acquisition rate of the high-quality pearl, and a new culture technique for improving the acquisition rate of the high-quality pearl is still required.

In consideration of the above circumstances, an object to be achieved by one aspect according to the present disclosure is to provide a pearl culture material, a nucleus insertion method, or a pearl culture material composition, with which an obtained pearl has a thick pearl layer and the acquisition rate of the high-quality pearl is improved.

Specific means for achieving the above object include the following aspects.

<1> A pearl culture material comprising at least one selected from the group consisting of a pearl nucleus and a mantle,
in which the at least one selected from the group consisting of a pearl nucleus and a mantle contains a protein having 10 EU/g or less of an endotoxin amount.

<2> The pearl culture material according to <1>, in which a coating amount of the protein in a surface area of the pearl nucleus or the mantle is 20 pg/mm$^2$ or more.

<3> The pearl culture material according to <1> or <2>, in which the endotoxin amount is 2.5 EU/g or less.

<4> The pearl culture material according to any one of <1> to <3>, in which the protein contains at least a part of an amino acid sequence of collagen.

<5> The pearl culture material according to <4>, in which the amino acid sequence of the collagen is an amino acid sequence of type I collagen α1 chain.

<6> The pearl culture material according to any one of <1> to <5>, in which the at least one selected from the group consisting of a pearl nucleus and a mantle contains a protein containing a repeating sequence of a GXY triplet which may be separated by one or more amino acids, and one or more RGD motifs, and having a polydispersity of less than 20.

<7> The pearl culture material according to any one of <1> to <6>, in which the protein has a weight-average molecular weight of 30 kDa to 200 kDa, which is determined by gel permeation chromatography.

<8> The pearl culture material according to any one of <1> to <7>, in which the protein includes a protein derived from a genetically recombinant yeast.

<9> A pearl culture material composition comprising the pearl culture material according to any one of <1> to <8>.

<10> A method of inserting a pearl nucleus into a pearl sag of a mother pearl oyster from which a pearl has been taken out, using the pearl culture material according to any one of <1> to <8>.

<11> A method of producing a pearl using a mother pearl oyster which is subjected to nucleus insertion by the method according to <10>.

According to one aspect according to the present disclosure, a pearl culture material, a nucleus insertion method, or a pearl culture material composition, with which an obtained pearl has a thick pearl layer and the acquisition rate of the high-quality pearl is improved is provided.

DESCRIPTION OF THE PREFERRED EMBODIMENTS

Hereinafter, the contents according to the present disclosure will be described in detail. The description of the constitutional requirements described below is based on the representative embodiments according to the present disclosure; however, the present disclosure is not limited to such embodiments.

In the present disclosure, a numerical range indicated using "to" means a range including numerical values described before and after "to" as a minimum value and a maximum value, respectively. In a numerical range described in a stepwise manner in the present disclosure, an upper limit value or a lower limit value described in a certain numerical range may be replaced with an upper limit value or a lower limit value of another numerical range described in a stepwise manner. Further, in the numerical ranges described in the present disclosure, the upper limit value or the lower limit value of a numerical range may be replaced with the value shown in Examples.

In the present disclosure, a combination of two or more preferred aspects is a more preferred aspect.

In the present disclosure, in a case where a plurality of substances corresponding to components are present in the composition, the amount of each component in the composition means a total amount of the plurality of substances present in the composition, unless otherwise noted.

In the present disclosure, the term "peptide" refers to a generic term for compounds formed by binding two or more amino acids through peptide bonds.

In the present disclosure, the term "polypeptide" refers to a generic term for compounds formed by peptide bonding of 10 or more amino acids. In a case where the number of amino acids is 10 or more, the "peptide" and the "polypeptide" can be used interchangeably.

In the present disclosure, the term "protein" refers to a polypeptide having a molecular weight of 5,000 or more. In a case where the molecular weight is 5,000 or more, the "protein" and the "polypeptide" can be used interchangeably.

In the present disclosure, the weight-average molecular weight (Mw) and the number-average molecular weight (Mn) of a protein are expressed in units of dalton (Da).

Unless otherwise specified, the weight-average molecular weight (Mw) and the number-average molecular weight (Mn) in the present disclosure are determined by using a gel permeation chromatography (may be also referred to as "gel permeation chromatography" or "GPC") analysis device (HLC-8220 GPC, manufactured by Tosoh Corporation) with a column of Shodex Asahipak GS-620 7G-p (manufactured by Showa Denko K.K.), which has an inner diameter of 7.5 mm and a length of 50 cm, and a solvent of 100 mM phosphate buffer (pH=6.9), carrying our detection with a differential refractometer, and carrying our the molecular weight conversion using pullulan as a standard substance.

In the present disclosure, the term "tackiness" means "pressure adhesiveness" or "stickiness" which is used in relation to the workability in a case of carrying out nucleus insertion of a pearl culture material.

In the present disclosure, "pearl covering" means the pearl layer thickness, and the pearl layer may be a mono-layer or a multi-layer. The pearl layer thickness may be measured from the thickness of the cross section of the pearl. The pearl layer thickness can be confirmed by subtracting the mass of the pearl nucleus before culture from the mass of the harvested pearl, and the larger this value is, the thicker the pearl layer is. In addition, it can be said that the thicker the pearl layer, the better the pearl covering.

In the present disclosure, "whiteness" is determined visually by an expert engaged in pearl culture; however, it can also be determined using a measuring device.

In the present disclosure, "high-quality pearl" refers to a pearl that satisfies at least the above description of "pearl layer is thick".

In the present disclosure, "stain" refers to a portion exhibited in blue, gray, or brown as compared with the overall color of the outer surface of the pearl. In the present disclosure, "scratches" refer to protrusions and dents formed on the surface of the pearl.

(Pearl Culture Material)

The pearl culture material according to the present disclosure contains at least one selected from the group consisting of a pearl nucleus and a mantle, and the at least one selected from the group consisting of a pearl nucleus and a mantle contains a protein having 10 EU/g or less of an endotoxin amount (hereinafter, also referred to as a "low endotoxin protein").

In a case where pearl culture is carried out using a pearl culture material containing a pearl nucleus and/or a mantle, which contains a low endotoxin protein, it is possible to improve the acquisition rate of the high-quality pearl of which the pearl covering is thick. In addition, it is possible to improve the acquisition rate of the high-quality pearl having a high whiteness.

In general, the pearl culture is a method in which a tissue piece of a mantle (a mantle piece) and a pearl nucleus are surgically inserted into the gonad of a mother pearl oyster in the body of the mother pearl oyster capable of producing a pearl, the tissue piece covers the surroundings of the nucleus to form a "pearl sag", and a secretion is secreted from epithelial cells of the mantle which forms the pearl sag to form a pearl layer on the surface of the pearl nucleus, whereby a pearl is produced.

In particular, the nucleus insertion is an operation of inserting a pearl nucleus into the body of the shell, which is a heavy burden on the mother pearl oyster, since the pearl nucleus obtained by spherically cutting a shell of other kinds of shellfishes is a foreign matter. The nucleus insertion is said to be an important process since the quality of the nucleus insertion technique affects the mortality of the shellfish after nucleus insertion and the quality of the pearl such as the presence or absence of stains and scratches on the pearl obtained.

Stains and scratches of the pearl are caused by an organic matter between the pearl nucleus and the pearl layer. As the causes of stains and scratches, it is said that the stains and scratches are derived from, for example, a tissue piece having a pigment of a blood cell or a germ cell, which becomes contained in the pearl sag, and an organic substance secreted by epithelial cells which have undergone inflammation ("Forefront of Pearl Research: Prospects for High Quality Pearl Production", published by Kouseisha Kouseikaku Co., Ltd., edited by Masahiko Awaji, Akira Furumaru, and Daisuke Matsubara, p33).

For the purpose of improving the survival rate of the shellfish and the rate of the high-quality pearl, the followings have been proposed; coating the pearl nucleus with a substance (for example, a peptide, fibronectin, chitosan, and a polylactic acid) that is expected to improve the biological compatibility between the living body of the shellfish and the pearl nucleus which is a foreign matter (see, for example, JP1989-148135A (JP-H01-148135A)), and a technique of adding an antibiotic when performing the above coating in order to kill bacteria considered to be one of the causes of an inflammatory reaction (see, for example, JP1990-203724A (JP-H02-203724A). Although the above technique improves pearl quality, the level of improvement is not sufficient, and thus the technique has not been widely used.

In order to further enhance the compatibility between the pearl nucleus and the living body of the shellfish, the inventors focused on endotoxin, which is released from bacteria and remains even after sterilization, and triggers a foreign matter reaction when entered the living body. Endotoxin is a lipopolysaccharide that constitutes the cell wall of Gram-negative bacteria, and it is known that even a very small amount of endotoxin causes various biological reactions such as fever in a case of entering the blood of mammals, but clear reports are not known on the influence on mollusks such as shellfish.

The inventors have found that in a case where a nucleus and/or a mantle coated with a protein having endotoxin as little as possible is used for nucleus insertion, the acquisition rate of the high-quality pearl in which pearl covering is thick and which is more value is improved. The inventors have also found that not only the stains and scratches on the pearl are reduced, but also the acquisition rate of the high-quality pearl having a further high whiteness is easily improved.

The reason why the above effects are obtained is not clear; however, the hypothesis for the reason is as follows.

It is presumed that in a case where a nucleus and/or a mantle coated with a protein having endotoxin as little as possible is used for nucleus insertion, the compatibility between a mother pearl oyster and a pearl nucleus is enhanced, whereby (1) a pearl sag is formed early, the pearl layer formation is started early, and thus covering becomes thick and pearl quality is improved. (2) It is presumed that in a pearl sag formed while suppressing the immune reaction, the covering becomes thicker because the secretion efficiency of a secretion that is used for forming a pearl layer, such as calcium carbonate or the like which is secreted from the tissue piece of the mantle, is improved, whereby covering becomes thick and pearl quality is improved.

In addition, it is presumed that a pearl sag is formed early by enhancing the compatibility between the mother pearl oyster and the pearl nucleus, the probability that germ cells become incorporated in the pearl layer is reduced, whereby stains and scratches are easily reduced. In addition, it is presumed that in the pearl sag formed by suppressing the immune reaction, an organic substance such as melanin pigment is not easily generated, whereby stains are easily reduced.

Hereinafter, each configuration constituting the pearl culture material according to the present disclosure will be described below.

<<Protein>>

The pearl culture material according to the present disclosure contains a pearl nucleus and a mantle, and at least one selected from the group consisting of a pearl nucleus and a mantle contains a protein (a "low endotoxin protein") having 10 EU/g or less of an endotoxin amount.

In a case where pearl culture is carried out using at least one selected from the group consisting of a pearl nucleus and a mantle, which contain the low endotoxin protein, it is possible to improve the acquisition rate of the high-quality pearl of which the pearl layer is thick.

From the viewpoint of further improving the acquisition rate of the high-quality pearl of which the pearl layer is thick, the endotoxin amount is preferably 8 EU/g or less, more preferably 6 EU/g or less, and still more preferably 2.5 EU/g or less. It is particularly preferable that endotoxin is substantially not contained.

The pearl nucleus and mantle in the pearl culture material according to the present disclosure may further contain a protein having an endotoxin amount exceeding 10 EU/g.

In the present specification, "EU/g" represents a measurement unit of endotoxin, and means a value determined based on the biological activity of standard endotoxin specified by the United States Pharmacopeia, and 1 EU/ml of endotoxin indicates about 0.1 ng/ml of endotoxin.

In the present disclosure, the endotoxin amount can be quantified by measuring with the kinetic turbidimetric method using a Lysate reagent (a Limulus reagent) (product name; "PYROGENT™ 5000", manufactured by LONZA).

From the viewpoint of further improving the acquisition rate of the high-quality pearl, the pearl culture material according to the present disclosure preferably contains a pearl nucleus containing a protein having 10 EU/g or less of an endotoxin amount.

The method of reducing the endotoxin amount contained in the pearl nucleus and the mantle to 10 EU/g or less is not particularly limited, and endotoxin contained in a protein such as natural gelatin, which is a raw material, may be reduced and removed by using a conventionally known method, for example, an adsorption method or ultrafiltration.

The low endotoxin protein may also be a protein derived from a genetically recombinant eukaryote. The low endotoxin protein is preferably a protein derived from a genetically recombinant eukaryote, rather than a low endotoxin protein purified from a protein such as natural gelatin which may contain endotoxin, from the viewpoint that the protein can be obtained in the absence of endotoxin.

Examples of the host of the genetically recombinant eukaryote include yeast, silk worm, a Chinese hamster ovary (CHO) cell, and an insect cell; however, the host is preferably yeast from the viewpoint that a high-productive strain is relatively easily acquired and the construction of mass production systems is relatively easy.

In the pearl nucleus and mantle, at least a part of the surface of the pearl nucleus and the mantle may be coated with the low endotoxin protein.

From the viewpoint of further improving the acquisition rate of the high-quality pearl, the coating percentage (the coating ratio) of the low endotoxin protein with respect to the total surface area of the pearl nucleus or the mantle is preferably 20% or more, more preferably 30% or more, still more preferably 40% or more, particularly preferably 50% or more, most preferably 60% or more, and extremely preferably 65% or more. The entire surface of the pearl nucleus or the mantle may be coated with the low endotoxin protein.

In the pearl nucleus and mantle contained in the pearl culture material according to the present disclosure, the protein coating amount in the total surface area of the pearl nucleus or the mantle is preferably 20 pg/mm$^2$ or more, more preferably 50 pg/mm$^2$ to 10,000 pg/mm$^2$, and still more preferably 50 pg/mm$^2$ to 500 pg/mm$^2$, from the viewpoint of further improving the acquisition rate of the high-quality pearl.

The coating amount of the low endotoxin protein in the surface area of the pearl nucleus or the mantle membrane is determined by dissolving and hydrolyzing the low endotoxin protein on the surface of the pearl nucleus or the mantle membrane, quantifying the amount of amino acid contained in the protein obtained by hydrolysis with liquid chromatography/mass spectrometry (LC/MS), and obtaining the difference between the amino acid amount obtained as above and the amino acid amount obtained by hydrolysis treatment of the pearl nucleus or the mantle, which is not coated with the protein.

More specifically, the coating amount can be determined by the following method.

(1) Elution of Surface Protein

For example, 10 pearl nuclei or 10 mantles are prepared, and the pearl nuclei or the mantles are immersed in about 10 mL of water at 20° C. and allowed to stand for 18 hours to prepare a sample solution of a culture material.

(2) Hydrolysis of Surface Protein

The culture material sample solution is concentrated with a centrifugal evaporator, 1 mL of 6 mol/L (N) hydrochloric acid is added to redissolve the solution, and the solution is allowed to stand at 110° C. for 22 hours.

(3) Redissolution of Protein

After the above 6 mol/L (N) hydrochloric acid is passed through nitrogen gas to be subjected to volatilization, 0.2 mL of 0.02 mol/L (N) dilute hydrochloric acid is further added.

(4) Quantification of Amino Acid by Liquid Chromatography/Mass Spectrometry (LC/MS)

Using a liquid chromatography/mass spectrometer (LC/MS) apparatus (UPLC/MS (SQD) manufactured by Waters Corporation), the amino acids contained in the sample are quantified under the following conditions, and the difference between the amino acid amount obtained as above and the amino acid amount of the blank nucleus or the blank mantle (the pearl nucleus or the mantle, which does not contain a low endotoxin protein).

Column: Intrade amino acid 75, manufactured by Imtakt Corporation MS Electrospray (ESI) (positive mode)

The kind of amino acid to be quantified can be appropriately selected depending on the kind of protein, and in a case where Cellnest (product name, manufactured by FUJIFILM Corporation) is used as the low endotoxin protein, it is preferable to quantify proline (Pro).

Regarding the method (hereinafter, also referred to as "coating method") of incorporating a low endotoxin protein into the pearl nucleus and the mantle according to the present disclosure, the coating of the pearl nucleus or the mantle may be carried out, for example, with a conventionally known coating method by preparing a solution (hereinafter, may be also referred to as a "coating solution") of a pearl culture material composition, which will be described later.

The coating method is not particularly limited, and examples thereof include a method of immersing a pearl nucleus or a mantle in a coating solution, a method of splaying a coating solution on a surface of a pearl nucleus or a mantle, and a method of coating a surface of a pearl nucleus or a mantle using a brush containing a coating solution.

The concentration of the low endotoxin protein contained in the coating solution is not particularly limited, and it is preferably 0.0001% by mass to 1% by mass and more preferably 0.0005% by mass to 0.5% by mass, with respect to the total mass of the coating solution.

The low endotoxin protein contained in the pearl culture material according to the present disclosure may be a freeze-dried product. In a case where the low endotoxin protein is a freeze-dried product, it is preferably a freeze-dried product that has been freeze-dried together with an activator described later.

The low endotoxin protein contained in the pearl culture substrate according to the present disclosure preferably contains at least a part of the amino acid sequence of collagen and more preferably the amino acid sequence of the collagen domain of collagen (that is, the domain forming a triple-stranded helix, hereinafter, also referred to simply as the "collagen domain").

The collagen domain includes a repeating sequence of the GXY triplet which may be separated by one or more amino acids, which will be described later, and one or more RGD motifs.

The percentage (total percentage) of the region occupied by the region derived from the amino acid sequence of collagen (for example, the amino acid sequence of SEQ ID NO: 1) with respect to the entire amino acid sequence of the low endotoxin protein is preferably 50% or more, more preferably 60% or more, still more preferably 70% or more, particularly preferably 80% or more, most preferably 90% or more, and extremely particularly preferably 95% or more.

The origin of collagen is not particularly limited, and collagen may be derived from any species. The collagen may be collagen derived from two or more species. Examples of the origin of collagen include fish (tilapia), cattle, pigs, and humans.

Collagen may be natural collagen contained in cowhide, pig skin, fish skin, or the like as described above; however, the collagen is preferably insoluble in a solvent such as water. For this reason, in a case where collagen is extracted, treatment such as the use of protein hydrolase or gelatinization by heating is required, and thus the molecular weight distribution of the obtained collagen is wide. In addition, since commercially available gelatin generally has a molecular weight distribution of several thousands to several millions, it is unlikely that the polydispersity is less than 20 even in a case where natural collagen is extracted by a general method.

In one embodiment according to the present disclosure, a low endotoxin protein obtained by subjecting collagen extracted from a natural collagen source derived from cow skin, pig skin, or fish skin, to a fractionation method such as size exclusion chromatography to separate and purify only protein molecules within a specific molecular weight range may be used.

In another embodiment according to the present disclosure, the low endotoxin protein can be obtained through the production by a recombinant cell into which a gene of a protein containing a repeating sequence of GXY triplets, which will be described later, and containing one or more RGD motifs has been introduced. In this case, as the host cell into which the gene of the low endotoxin protein is introduced, a bacterial cell such as Escherichia coli, a yeast cell such as S. cerevisiae, or insect cell such as a silk worm cell can be used; however, from the viewpoint of reducing the endotoxin amount, the host is preferably a yeast cell, and the low endotoxin protein is preferably a protein derived from a genetically recombinant yeast.

As an expression vector, an appropriate vector may be selected from known vectors and used depending on the host and the size of the protein to be introduced. In a case where the low endotoxin protein is produced by a recombinant cell, a protein having high molecular weight uniformity can be obtained.

The type of collagen is not particularly limited and may be any type of collagen. Examples of the collagen include type I collagen, type II collagen, type III collagen, type IV collagen, type V collagen, type VI collagen, type VII collagen, type VIII collagen, type IX collagen, type X collagen, type XI collagen, type XII collagen, type XIII collagen, type XIV collagen, type XV collagen, type XVI collagen, type XVII collagen, type XVIII collagen, type XIX collagen, type XX collagen, type XXI collagen, type XXII collagen, type XXIII collagen, type XXIV collagen, type XXV collagen, type XXVI collagen, type XXVII collagen, and type XXVIII collagen.

The amino acid sequence of the collagen may be an amino acid sequence of any subtype of a plurality of polypeptides constituting the collagen. For example, in a case of type I collagen, the amino acid sequence of the collagen may be the amino acid sequence of type I collagen α1 chain or the amino acid sequence of type I collagen α2 chain; and in a case of type V collagen, the amino acid sequence of the collagen may be the amino acid sequence of type V collagen α1 chain, the amino acid sequence of type V collagen α2 chain, or the amino acid sequence of type V collagen α3 chain.

Among them, the amino acid sequence of the collagen is preferably the amino acid sequence of type I collagen and more preferably the amino acid sequence of type I collagen α1 chain, in terms of the availability of natural collagen in a case of natural collagen and in terms of the production result in a case of the genetically recombinant collagen.

The low endotoxin protein is preferably a polypeptide including the amino acid sequence of SEQ ID NO: 1 and more preferably a polypeptide made up of the amino acid sequence of SEQ ID NO: 1.

The low endotoxin protein contained in the pearl nucleus or the mantle may be a single polypeptide or a combination of two or more polypeptides.

The amino acid sequence of human type I collagen α1 chain set forth in SEQ ID NO: 2 contains only two RGD sequences (a sequence of amino acids at positions 745 to 747 and a sequence of amino acids at positions 1093 to 1095) in the total length of 1464 amino acids. In a case where a protein prepared based on the amino acid sequence of human type I collagen α1 chain is used as the protein according to the present disclosure, a protein having a more preferable cell adhesion promoting ability is obtained by changing the number of RGD sequences to the preferred range described above.

In addition, it is considered that the removal of telopeptides present at both ends of the molecule and contributing to the association between collagen molecules results in the suppression of association between the molecules and the further improved workability at the time of nucleus insertion.

From the viewpoints described above, the low endotoxin protein contained in the pearl culture material according to the present disclosure may be, for example, a protein including a plurality of regions (preferably 4 to 20 regions and more preferably 6 to 16 region) having an amino acid length of 20 amino acids to 60 amino acids including Arg at position 745 to Asp at position 747 in the amino acid sequence of SEQ ID NO: 2. In this case, the plurality of regions each may be the same or different (in other words, the regions around the RGD at positions 745 to 747 overlap but the boundary points are different) and may be in direct contact with each other or one or more other amino acid residues may be interposed therebetween.

Each of the regions is preferably a region having an amino acid length of 34 amino acids to 50 amino acids including a region of Gly at position 722 to Gly at position 755 independently of each other. In addition, the total amino acid length is preferably 200 amino acids to 800 amino acids and more preferably 300 amino acids to 600 amino acids, from the viewpoint of expression efficiency in recombinant cells, solubility in water, and suppression of deliquescence.

More specifically, the low endotoxin protein contained in the pearl culture material according to the present disclosure may be the protein set forth in SEQ ID NO: 1. This protein is a 571 amino acid long protein including 12 regions of about several tens of amino acids including Arg at position 745 to Asp at position 747 in SEQ ID NO: 2.

The protein constituting the low endotoxin protein preferably contains a repeating sequence of GXY triplets which may be separated by one or more amino acids, and one or more RGD motifs, and preferably has a polydispersity of less than 20.

—GXY Triplet—

In the present disclosure, the term "GXY triplet" refers to a unit of an amino acid sequence in which three amino acids "G (glycine)", "X (any amino acid other than G)", and "Y (any amino acid other than G)" are present from an N-terminal side to a C-terminal side.

Here, "X" and "Y" each independently represent any amino acid other than G. The "X" and/or "Y" is preferably "P (proline)" and/or "4-hydroxyproline".

The percentage (total percentage) of the region occupied by the GXY triplet with respect to the entire amino acid sequence of the protein according to the present disclosure is preferably 50% or more, more preferably 60% or more, still more preferably 70% or more, particularly preferably 80% or more, most preferably 90% or more, and extremely particularly preferably 95% or more.

In addition, the GXY triplet may be repeated over the entire length of the amino acid sequence of the low endotoxin protein.

In a case where the GXY triplet is present, the low endotoxin protein has a structure similar to a collagen protein having high biocompatibility. For this reason, it is considered that the acquisition rate of the high-quality pearl is improved in a case where at least one selected from the group consisting of a pearl nucleus and a mantle, which contain the low endotoxin protein, is nucleus-inserted.

In the present disclosure, the "GXY triplet" may be connected in series without containing an amino acid between the GXY triplets, and one or more amino acids may be contained between the GXY triplets. Preferably, the "GXY triplet" is connected in series without including an amino acid between the GXY triplets.

—RGD Motif—

In the present disclosure, the term "RGD motif" refers to a motif in which three amino acids "R (arginine)", "G (glycine)", and "D (aspartic acid)" are present from an N-terminal side to a C-terminal side. Since the "RGD motif" is involved in cell adhesion, it is considered that in a case where the pearl nucleus containing the low endotoxin protein is nucleus-inserted, the extension of mantle cell to the surface of the pearl nucleus is promoted, and thus a high-quality pearl having few stains are generated.

The term "motif" used in relation to a protein refers to an amino acid sequence having a functional or structural characteristic.

The number of "RGD motifs" in the low endotoxin protein may be 1 to 100, preferably 5 to 75, more preferably 10 to 50, and still more preferably 10 to 25.

The "RGD motif" is preferably contained at a rate of 1 motif with respect to 10 to 100 amino acids constituting the low endotoxin protein, more preferably at a rate of 1 motif with respect to 20 to 75 amino acids constituting the low endotoxin protein, still more preferably at a rate of 1 motif with respect to 30 to 60 amino acids constituting the low endotoxin protein, and even still more preferably at a rate of 1 motif with respect to 45 to 55 amino acids constituting the low endotoxin protein.

In a case where the RGD motif is contained in the low endotoxin protein in the above range, the cell adhesion promoting ability is enhanced, which can contribute to the acquisition rate of the high-quality pearl.

The "GXY triplet" and the "RGD motif" can exist in an overlapping manner. That is, the first G of the GXY triplet may be the second G of the RGD motif.

The weight-average molecular weight of the low endotoxin protein is preferably 30 kDa (kilodalton) to 200 kDa, more preferably 30 kDa to 100 kDa, still more preferably 40 kDa to 75 kDa, and particularly preferably 50 kDa to 60 kDa. In a case where the weight-average molecular weight of the low endotoxin protein is within the above range, the balance between good solubility in water and suppression of deliquescence due to moisture absorption is excellent.

The number-average molecular weight of the low endotoxin protein is preferably 15 kDa to 100 kDa, more preferably 20 kDa to 80 kDa, still more preferably 30 kDa to 60 kDa, and particularly preferably 40 kDa to 50 kDa, from the viewpoint that the balance between good solubility in water and suppression of deliquescence due to moisture absorption is excellent.

—Polydispersity—

The polydispersity of the low endotoxin protein is preferably less than 20, more preferably less than 10, still more preferably less than 5, and particularly preferably less than 2, from the viewpoint of further improving the acquisition rate of the high-quality pearl and being excellent operability at the time of nucleus insertion.

It is considered that, in a case where the polydispersity of the low endotoxin protein is in the above range, the interaction between the pearl nucleus and the mantle tissue in a mother pearl oyster at a biological tissue level can be equalized, whereby the acquisition rate of the high-quality pearl is further improved. In addition, it is considered that a bond due to the intermolecular interaction between molecules is formed preferentially over the bond between polar hydrophilic groups, and thus the absorption of moisture in the air, which is a main cause of tackiness, is inhibited and the operability at the time of nucleus insertion is excellent.

In the present disclosure, the polydispersity means a value (Mw/Mn) obtained by dividing a weight-average molecular weight (Mw) by a number-average molecular weight (Mn).

<Pearl Nucleus>

The pearl culture material according to the present disclosure includes a pearl nucleus. In general, in a case where the pearl nucleus is nucleus-inserted together with the mantle into the inside of the mother pearl oyster, a secretion containing calcium carbonate as the main component is secreted from epithelial cells of the mantle, thereby forming the pearl layer on the surface of the pearl nucleus.

The material for the pearl nucleus is not particularly limited as long as a pearl layer is formed on the surface of the pearl nucleus, examples thereof include the genus Lamprotula, pig-toe mussel (*Fusconaia flava*), and niggerhead mussel (*Fusconaia ebenus*), which are freshwater bivalves. Further, as the material for the pearl nucleus, a resin such as polypropylene or polycarbonate, glass, quartz, or ceramics such as calcium carbonate may be used as the material.

The size (the maximum diameter) of the pearl nucleus may be appropriately selected according to a desired size of the pearl and may be, for example, 4 mm to 10 mm.

The shape of the pearl nucleus is not particularly limited and may be a spherical shape, a hemispherical shape, an elliptical shape, a cocoon-shape, a disk shape, a star shape, a teardrop shape, an undetermined shape, or the like.

<Mantle>

The pearl culture material according to the present disclosure includes a mantle. The mantle is a small piece of mantle (hereinafter, also referred to as "mantle piece") of the shellfish, and in a case where the mantle is nucleus-inserted together with the pearl nucleus into the inside of the mother pearl oyster, a secretion containing calcium carbonate as the main component is secreted from epithelial cells of the mantle, thereby forming the pearl layer on the surface of the pearl nucleus.

The shellfish that is used to prepare the mantle is not particularly limited, and examples thereof include *Pinctada martensii*, *Pteria penguin*, *Pinctada maxima*, *Pinctada margaritifera*, snails such as Ezo-abalone, conch, pink conch, *Pleuroploca gigantea*, and melon shell, and freshwater shellfishes such as *Hyriopsis schlegelii*, *Hyriopsis cumingii*, and *Cristaria plicata*. The mantle may be derived from the shellfish of the same species as the mother pearl oyster or may be derived from a shellfish whose species is different from that of the mother pearl oyster.

In the present disclosure, the description of the "shellfish whose species is different from that of a mother pearl oyster" indicates that the "shellfish whose species is different from that of a mother pearl oyster" includes not only a shellfish whose species is different from that of the mother pearl oyster in terms of the taxonomic species but also a shellfish whose variety or lineage is different from that of the mother pearl oyster, although the shellfish is classified in the same category as the mother pearl oyster in terms of taxonomy.

In a case where a mantle derived from a shellfish whose species is different from that of the mother pearl oyster (hereinafter, also referred to as "heterogeneous mantle") is used, examples of the combination of the mother pearl oyster and the heterogeneous mantle include a combination in which the mother pearl oyster is *Pinctada martensii* and the heterogeneous is *Pteria penguin*; a combination in which the mother pearl oyster is *Pinctada martensii* and the heterogeneous is a snail; and a combination in which the mother pearl oyster is *Pinctada martensii* and the heterogeneous is a freshwater shellfish.

The kind of mother pearl oyster which is subjected to nucleus insertion of the pearl culture material according to the present disclosure is not particularly limited, and examples thereof include shellfishes the same as those which are used for preparing a mantle, and any shellfish can be preferably used.

The size of the mantle may be appropriately selected according to the size of the pearl nucleus and is, for example, about 2 mm to 4 mm square (2 mm×2 mm to 4 mm×4 mm).

(Method of Carrying Out Nucleus Insertion of Pearl Nucleus)

The method of inserting a pearl nucleus according to the present disclosure may be a method of inserting (hereinafter, may be referred to nucleus reinsertion) a pearl nucleus into the pearl sag of the mother pearl oyster from which a pearl has been taken out by using the pearl culture material according to the present disclosure.

The method of forming a pearl in the mother pearl oyster is not particularly limited, and the pearl may be formed by a general pearl culture method or formed in an artificial environment described later.

The method of inserting a pearl nucleus according to the present disclosure can be applied to the method of forming a pearl in an in vitro system such as in a test tube system, in a reactor system, or in a cell culture medium system and carrying out nucleus insertion of the pearl into the pearl sag of the mother pearl oyster from which a pearl has been taken out. In this case, the mother pearl oyster from which a pearl is taken out and the mother pearl oyster which is subjected to nucleus reinsertion may be the same species or species different from each other.

In the method of inserting a pearl nucleus according to the present disclosure, the mother pearl oyster is not particularly limited, and examples thereof include the shellfishes that are used for preparing the above-mentioned mantle. In addition, the mother pearl oyster which is subjected to nucleus reinsertion is not particularly limited, and examples thereof include seawater shellfishes such as *Pinctada martensii*, *Pinctada maxima*, and *Pinctada margaritifera*, and freshwater shellfishes such as *Hyriopsis cumingii*. Any one of these shellfish can be preferably subjected to nucleus reinsertion.

In addition, the method of producing a pearl according to the present disclosure may be a method of producing a pearl using the mother pearl oyster which has been subjected to nucleus insertion by the nucleus reinsertion method according to the present disclosure.

The method of producing a pearl is not particularly limited, and the pearl may be produced by a typical pearl culture method or may be produced in an artificial environment, for example, in an in vitro system such as in a test tube system, in a reactor system, or in a cell culture medium system.

Further, as one embodiment of the pearl culture material according to the present disclosure, the mother pearl oyster may be subjected to nucleus insertion of a mantle which does not contain a protein having 10 EU/g or less of an endotoxin amount, by using the pearl culture material according to the present disclosure.

<Pearl Culture Material Composition>

The pearl culture material composition according to the present disclosure includes the pearl culture material according to the present disclosure. In a case where pearl culture is carried out using the pearl culture material composition according to the present disclosure, it is possible to improve the acquisition rate of the high-quality pearl.

The shape of the pearl culture material composition is not particularly limited and may be liquid, solid, or semi-solid.

As long as the effects according to the present disclosure are not impaired, the pearl culture material composition according to the present disclosure may contain the following additives; an excipient, a solvent, an inorganic salt such as NaCl, a buffer such as HEPES or PBS, a thickener, a pH adjuster, a stabilizer, a light absorber, an antibiotic such as a penicillin-based compound, a cephem-based compound, a macrolide-based compound, a tetracycline-based compound, or a new quinolone-based compound, and a colorant such as phenol red or eosin.

The solvent is not particularly limited, and examples thereof include water, an alcohol compound, an animal and vegetable oil such as soybean oil or olive oil, a mineral oil, and a synthetic oil.

Among these, the solvent is preferably water from the viewpoint of excellent compatibility with the low endotoxin protein.

The excipient is not particularly limited, and examples thereof include a sugar compound such as maltose, inositol, mannitol, lactose, sucrose, or trehalose, an amino acid compound such as phenylalanine, a cellulose derivative such as hydroxypropyl cellulose, and an organic salt such as magnesium stearate.

In a case where the shape of the pearl culture material composition is solid, the low endotoxin protein is dissolved in an appropriate dissolution solution selected appropriately, and then at least one selected from the pearl nucleus and the mantle may be coated with the prepared solution.

The dissolution solution is preferably, for example, physiological saline, a variety of buffers, a solution of a saccharide such as glucose, inositol, mannitol, or lactose, or a glycol such as ethylene glycol or polyethylene glycol.

In addition, in a case where the low endotoxin protein contained in the pearl culture material composition according to the present disclosure is a freeze-dried product, the pearl culture material composition preferably further contains a suitable dissolution solution, for example, a liquid such as sterile water, physiological saline, a glucose solution, an electrolyte solution, or an amino acid solution.

The component contained in the pearl culture material composition according to the present disclosure is preferably a component whose endotoxin amount is reduced.

EXAMPLES

Hereinafter, the present disclosure will be described more specifically with reference to Examples, but the present disclosure is not limited to the following Examples as long as the gist of the present invention is not exceeded. Unless otherwise specified, "parts" and "%" are based on mass.

Aqueous coating solutions 1 to 7 were prepared as follows. The endotoxin amount of the Cellnest human type I collagen-like recombinant peptide (product name; Cellnest, freeze-dried product, manufactured by FUJIFILM Corporation) used below was below the detection limit (2.5 EU/g or less) as measured by the method of measuring the endotoxin amount described above ("PYROGENT' 5000", manufactured by LONZA"; the kinetic turbidimetric method).

The Cellnest human type I collagen-like recombinant peptide (hereinafter, may be simply referred to as the "collagen-like peptide" used below has a structure in which a site containing an RGD sequence having high cell adhesiveness is cut out from human type I collagen α1 chain into four patterns of fragments which are then linked to each other, and the resulting three linked structures of four patterns of fragments are further linked. More specifically, it has the amino acid sequence set forth in SEQ ID NO: 1, is composed of 571 amino acids, in which the GXY triplet is repeated, and contains 12 RGD motifs.

The weight-average molecular weight (Mw), the number-average molecular weight (Mn), the polydispersity (Mw/Mn), and the viscosity of the collagen-like peptide used below were measured according to the following methods.

An aqueous solution of the Cellnest human type I collagen-like recombinant peptide (manufactured by FUJIFILM Corporation) (after thawing for a frozen preparation) was heated at 40° C. for 30 minutes such that the collagen-like peptide was completely dissolved, diluted with 100 mM phosphate buffer such that the concentration of the protein in the aqueous solution was 0.2% by mass, and then filtered through a 0.45 μm filter to prepare a sample solution.

The above sample solution was measured using a high-speed gel permeation chromatography (GPC) analysis apparatus (product name; HLC-8220GPC, manufactured by Tosoh Corporation) under the following conditions, the weight-average molecular weight (Mw) and the number-average molecular weight (Mn) was determined in terms of pullulan, and the polydispersity (Mw/Mn) was calculated from the determined weight-average molecular weight and the number-average molecular weight. The results were as follows.

Weight-average molecular weight (Mw); 56,494
Number-average molecular weight (Mn); 48,787
Polydispersity (Mw/Mn); 1.16
—GPC Measurement Conditions—
Column: Shodex Asahipak GS-620 7G-p, inner diameter: 7.5 mm, length: 50 cm (manufactured by Showa Denko K.K.)
Eluent: 100 mM phosphate buffer (pH=6.9)
Flow rate: sample: 1.0 mL/min, reference: 0.1 mL/min
Column temperature (setting): 40° C.
Injection volume: 100 μL
Detector: RI/UV (210 nm)
Carbohydrate for molecular weight calibration: pullulan (Shodex P-82, manufactured by Showa Denko K.K.)

<<Preparation of Coating Solution 1>>

100 mg of the Cellnest human type I collagen-like recombinant peptide (product name; Cellnest, freeze-dried product, manufactured by FUJIFILM Corporation) was added to water for injection (manufactured by Hikari Pharmaceutical Co., Ltd.) to prepare a 0.1% by mass aqueous coating solution 1. The Cellnest human type I collagen-like recombinant peptide has the amino acid sequence of SEQ ID NO: 1.

<<Preparation of Coating Solution 2>>

100 mg of the Cellnest human type I collagen-like recombinant peptide (product name; Cellnest, freeze-dried product, manufactured by FUJIFILM Corporation) and endotoxin [standard endotoxin described in the Japanese Pharmacopoeia, manufactured by the Pharmaceutical and Medical Device Regulatory Science Society of Japan] was added to water for injection (manufactured by Hikari Pharmaceutical Co., Ltd.) to prepare a 0.1% by mass aqueous coating solution 2 in which the endotoxin amount of the recombinant peptide was 5 EU/g.

<<Preparation of Coating Solution 3>>

In the preparation of the above coating solution 2, a 0.1% by mass aqueous coating solution 3 in which the endotoxin amount of the recombinant peptide was 10 EU/g was prepared in the same manner as the coating solution 2 except that the addition amount of endotoxin [standard endotoxin described in the Japanese Pharmacopoeia, manufactured by the Pharmaceutical and Medical Device Regulatory Science Society of Japan] was changed to the amount shown in Table 1.

<<Preparation of Coating Solution 4>>

In the preparation of the above coating solution 2, a 0.1% by mass aqueous coating solution 4 in which the endotoxin amount of the recombinant peptide was 30 EU/g was prepared in the same manner as the coating solution 2 except that the addition amount of endotoxin [standard endotoxin described in the Japanese Pharmacopoeia, manufactured by the Pharmaceutical and Medical Device Regulatory Science Society of Japan] was changed to the amount shown in Table 1.

<<Preparation of Coating Solution 5>>

In the preparation of the above coating solution 2, a 0.1% by mass aqueous coating solution 5 in which the endotoxin amount of the recombinant peptide was 100 EU/g was prepared in the same manner as the coating solution 2 except that the addition amount of endotoxin [standard endotoxin described in the Japanese Pharmacopoeia, manufactured by the Pharmaceutical and Medical Device Regulatory Science Society of Japan] was changed to the amount shown in Table 1.

<<Preparation of Coating Solution 6>>

In the preparation of the above coating solution 2, a 0.1% by mass aqueous coating solution 6 in which the endotoxin amount of the recombinant peptide was 1,000 EU/g was prepared in the same manner as the coating solution 2 except that the addition amount of endotoxin [standard endotoxin described in the Japanese Pharmacopoeia, manufactured by the Pharmaceutical and Medical Device Regulatory Science Society of Japan] was changed to the amount shown in Table 1.

<<Preparation of Coating Solution 7>>

In the preparation of the above coating solution 2, a 0.1% by mass aqueous coating solution 7 in which the endotoxin amount of the recombinant peptide was 10,000 EU/g was prepared in the same manner as the coating solution 2 except that the addition amount of endotoxin [standard endotoxin described in the Japanese Pharmacopoeia, manufactured by the Pharmaceutical and Medical Device Regulatory Science Society of Japan] was changed to the amount shown in Table 1.

<<Preparation of Coated Nucleus 1>>

An untreated nucleus (pearl nucleus) having a size of about 7 mm in diameter, which had been washed and sterilized, was completely immersed in the aqueous coating solution 1 prepared as described above, and then subjected to shaking and stirring at 37° C. for 2 hours. Then, the mixture was filtered through a metal colander (16 mesh) and then dried under an atmosphere of a temperature of 25° C. and a humidity of 55% for 24 hours to prepare a coated nucleus 1.

The amount of recombinant peptide applied onto the surface of the coated nucleus 1 was measured by the following method and found to be 339 pg/mm$^2$.

—Method of Measuring Coating Amount of Recombinant Peptide—

(1) Elution of Surface Protein

At least 10 pearl nuclei or 10 mantles were prepared, and the pearl nuclei or the mantles were immersed in about 10 mL of water and allowed to stand for 18 hours to prepare a sample solution of a culture material.

(2) Hydrolysis of Surface Protein 1 mL of 6 mol/L (N) hydrochloric acid was added to the culture material sample solution, and the mixture was allowed to stand at 110° C. for 22 hours.

(3) Redissolution of Protein

After 6 mol/L (N) hydrochloric acid was passed through nitrogen gas to be subjected to volatilization, 0.2 mL of 0.02 mol/L (N) dilute hydrochloric acid was further added.

(4) Quantification of Amino Acid by LC/MS

Proline was quantified using LC/MS (model number; UPLC/MS (SQD), manufactured by Waters Corporation), the difference between the proline amount obtained and the proline amount of the blank nucleus (the pearl nucleus which does not contain a low endotoxin protein) was determined, the peptide amount was determined from the calibration curve prepared in advance, and the coating amount per 1 $mm^2$ was determined.

<<Preparation of Coated Nuclei 2 to 7>>

In the preparation of the coated nuclei 1, coated nuclei 2 to 7 were prepared in the same manner as the coated nuclei 1 except that the aqueous coating solution 1 was changed to the aqueous coating solutions 2 to 7.

Examples 1-1 to 1-3 and Comparative Examples 1-1 to 1-5

The following culture experiments were carried out using the coated nuclei 1 to 7 prepared above. The harvested pearls were evaluated for (1) to (3) below, and the evaluation results are shown in Table 1.

[Culture Experiment]

Approximately 140 mother pearl oysters of *Pinctada martensii* (natural shellfishes, 2 years old) were prepared as one group, subjected to nucleus insertion using the coated nuclei and mantle prepared above, and then cultured. Eight months after the nucleus insertion and the culture, the nucleus was extracted from the mother pearl oyster, and the pearls were harvested.

(1) Product Pearl Acquisition Rate

An expert engaged in pearl culture visually sorted the harvested pearls to the first-class products, second-class products, and defective beads. The first-class and second-class pearls are high-quality pearls and are at an acceptable level as commercial products.

The rate of the number of the sorted first-class and second-class pearls to the number of the harvested pearls was defined as the "product rate (the product rate 1) to the number of the harvested pearls". In addition, the rate of the number of the sorted first-class and second-class pearls to the number of inserted nuclei was defined as the "product rate (product rate 2) to the number of inserted nuclei". The larger the value of the product rate 1 and the product rate 2, the better the product pearl acquisition rate.

(2) Pearl Layer Thickness (Covering)

The average mass of the pearls was determined by subtracting the mass of the pre-cultured pearl nucleus measured in advance from the mass of the harvested pearl and obtaining the mass of the formed pearl layer of each pearl. The larger the average mass value of the pearl layer, the thicker the pearl layer and the better the "covering".

(3) Whiteness

The whiteness was evaluated using only the first-class pearls sorted in (1) above. The expert in (1) above visually compared the whiteness of the first-class pearls and the standard pearls, evaluated each first-class pearl based on the following criteria, and the average value of the respective evaluation values was calculated and used as the whiteness. The larger the value of whiteness, the better the whiteness.

—Evaluation Criteria—

1: The appearance of the pearl is bluish and cream-colored, and both bleaching and toning are necessary for processing into jewelry.

2: The appearance of the pearl is cream-colored, bleaching is necessary for processing into jewelry, but toning is not necessary.

3: The appearance of the pearl is very pale cream-colored, and neither bleaching treatment nor toning is necessary for processing into jewelry.

TABLE 1

| | Pearl culture material | | Inserted nuclei | Harvested pearl | Survival rate | First-class product | Second-class product |
|---|---|---|---|---|---|---|---|
| | Pearl nucleus | Mantle | (nucleus) | (pearl) | (%) | (pearl) | (pearl) |
| Example 1-1 | Coated nucleus 1 (without endotoxin) | Absent | 144 | 114 | 79 | 48 | 53 |
| Example 1-2 | Coated nucleus 2 (endotoxin: 5 EU/g) | Absent | 140 | 110 | 79 | 40 | 54 |
| Example 1-3 | Coated nucleus 3 (endotoxin: 10 EU/g) | Absent | 144 | 113 | 78 | 38 | 54 |
| Comparative Example 1-1 | Coated nucleus 4 (endotoxin: 30 EU/g) | Absent | 144 | 109 | 76 | 13 | 55 |
| Comparative Example 1-2 | Coated nucleus 5 (endotoxin: 100 EU/g) | Absent | 143 | 109 | 76 | 13 | 56 |
| Comparative Example 1-3 | Coated nucleus 6 (endotoxin: 1,000 EU/g) | Absent | 144 | 95 | 66 | 6 | 38 |

TABLE 1-continued

| | | | | | | | |
|---|---|---|---|---|---|---|---|
| Comparative Example 1-4 | Coated nucleus 7 (endotoxin: 10,000 EU/g) | Absent | 144 | 90 | 63 | 1 | 35 |
| Comparative Example 1-5 | Absent | Absent | 150 | 100 | 67 | 8 | 42 |

| | Defective bead (bead) | First-class product rate (%) | Acquisition rate of high-quality pearl | | Covering/pearl layer thickness (g) | Whiteness |
|---|---|---|---|---|---|---|
| | | | Product rate 1 (%) | Product rate 2 (%) | | |
| Example 1-1 | 13 | 42 | 89 | 70 | 0.287 | 2.7 |
| Example 1-2 | 16 | 36 | 85 | 67 | 0.282 | 2.3 |
| Example 1-3 | 21 | 34 | 81 | 64 | 0.279 | 2.3 |
| Comparative Example 1-1 | 41 | 12 | 62 | 47 | 0.247 | 1.6 |
| Comparative Example 1-2 | 40 | 12 | 63 | 48 | 0.236 | 1.4 |
| Comparative Example 1-3 | 51 | 6 | 46 | 31 | 0.230 | 1.3 |
| Comparative Example 1-4 | 54 | 1 | 40 | 25 | 0.232 | 1.0 |
| Comparative Example 1-5 | 50 | 8 | 50 | 33 | 0.233 | 1.5 |

<<Preparation of Coated Mantles 1 to 7>>

A mantle piece cut into 2 mm squares (2 mm×2 mm) was completely immersed in the aqueous coating solution 1 prepared above at 25° C. for 1 minute to prepare a coated mantle 1.

In addition, coated mantles 2 to 7 were prepared in the same manner as in the preparation of the coated mantle 1 except that the aqueous coating solution 1 was changed to the aqueous coating solutions 2 to 7.

Using the obtained coated mantles 1 to 7 and untreated nuclei, the same culture experiment as in Example 1-1 was carried out. In the culture experiment using the coated mantles 1 to 3, the obtained pearls had a thick pearl layer and were excellent in covering as in Example 1-1. The whiteness was also excellent.

On the other hand, in the culture experiment using the coated mantles 4 to 7, the obtained pearls were inferior in the pearl layer thickness and whiteness as in Comparative Example 1-1.

Further, when the same culture experiment as in Example 1-1 was carried out by combining the coated nucleus 1 and the coated mantle 1, the obtained pearls had a thick pearl layer and were excellent in covering as in Example 1-1. The whiteness was also excellent.

<<Preparation of Coating Solution 21>>

2,000 mg of the Cellnest human type I collagen-like recombinant peptide (product name; Cellnest, freeze-dried product, manufactured by FUJIFILM Corporation) was added to water for injection (manufactured by Hikari Pharmaceutical Co., Ltd.) to prepare a 1% by mass aqueous coating solution 21.

<<Preparation of Coating Solution 22>>

100 mg of the Cellnest human type I collagen-like recombinant peptide (product name; Cellnest, freeze-dried product, manufactured by FUJIFILM Corporation) was added to water for injection (manufactured by Hikari Pharmaceutical Co., Ltd.) to prepare a 0.025% by mass aqueous coating solution 22.

<<Preparation of Coating Solution 23>>

100 mg of the Cellnest human type I collagen-like recombinant peptide (product name; Cellnest, freeze-dried product, manufactured by FUJIFILM Corporation) was added to water for injection (manufactured by Hikari Pharmaceutical Co., Ltd.) to prepare a 0.0125% by mass aqueous coating solution 23.

<<Preparation of Coating Solution 24>>

100 mg of the Cellnest human type I collagen-like recombinant peptide (product name; Cellnest, freeze-dried product, manufactured by FUJIFILM Corporation) was added to water for injection (manufactured by Hikari Pharmaceutical Co., Ltd.) to prepare a 0.0625% by mass aqueous coating solution 24.

<<Preparation of Coated Nuclei 21 to 24>>

In the preparation of the coated nucleus 1, coated nuclei 21 to 24 were prepared in the same manner as the coated nuclei 1 except that the aqueous coating solutions 21 to 24 were used instead of the aqueous coating solution 1. The amount of recombinant peptide applied onto the surface of each of the obtained coated nuclei 21 to 24 was measured according to the same procedure as the above method. The coating amount of the recombinant peptide in the coated nuclei 21 to 24 was as follows.

Coating amount of recombinant peptide of coated nucleus 21; 20,130 pg/mm$^2$

Coating amount of recombinant peptide on coated nucleus 22; 147 pg/mm$^2$

Coating amount of recombinant peptide on coated nucleus 23; 83 pg/mm$^2$

Coating amount of recombinant peptide on coated nucleus 24; 29 pg/mm$^2$

Examples 2-1 to 2-4

Using the coated nuclei 21 to 24 prepared above, the culture experiment was carried out in the same manner as in Example 1-1, and the harvested pearls were used for evaluation in the same manner as in Example 1. The evaluation results are described in Table 2.

TABLE 2

| | Pearl culture material | | Inserted nuclei | Harvested pearl | Survival rate | First-class product | Second-class product | De-fective bead | First-class product rate | Acquisition rate of high-quality pearl | | Covering/pearl layer thickness | White-ness |
|---|---|---|---|---|---|---|---|---|---|---|---|---|---|
| | | | | | | | | | | Product rate 1 | Product rate 2 | | |
| | Pearl nucleus | Mantle | (nucleus) | (pearl) | (%) | (pearl) | (pearl) | (bead) | (%) | (%) | (%) | (g) | ness |
| Example 2-1 | Coated nucleus 21 (coating amount: 20,130 pg/mm$^2$) | Absent | 144 | 113 | 78 | 42 | 53 | 18 | 84 | 37 | 66 | 0.284 | 2.7 |
| Example 2-2 | Coated nucleus 22 (coating amount: 147 pg/mm$^2$) | Absent | 144 | 114 | 79 | 49 | 51 | 14 | 88 | 43 | 69 | 0.287 | 2.6 |
| Example 2-3 | Coated nucleus 23 (coating amount: 83 pg/mm$^2$) | Absent | 144 | 109 | 76 | 40 | 52 | 17 | 84 | 37 | 64 | 0.271 | 2.2 |
| Example 2-4 | Coated nucleus 24 (coating amount: 29 pg/mm$^2$) | Absent | 144 | 111 | 77 | 39 | 51 | 21 | 81 | 35 | 63 | 0.270 | 2.2 |

From the results shown in Tables 1 and 2, it is revealed that in a case where the pearl culture material according to the present disclosure is used, the obtained pearl has a thick pearl layer, that is, is excellent in "covering" as compared with the pearl culture material of Comparative Examples. Further, in a case where the pearl culture material according to the present disclosure is used, the obtained pearl is excellent in "whiteness" and the rate (the product rate) of the number of products to the number of inserted nuclei and the number of harvested pearls as compared with the pearl culture material of Comparative Examples. In a case where pearls are cultured using the pearl culture material according to the present disclosure, the high-quality pearl can be obtained.

The disclosure of JP2018-193668 filed on Oct. 12, 2018, is incorporated in the present specification by reference in its entirety.

All documents, patent applications, and technical standards described in the present specification are incorporated in the present specification by reference, to the same extent as in the case where each of the documents, patent applications, and technical standards is specifically and individually described.

What is claimed is:

1. A pearl culture material comprising at least one selected from the group consisting of a pearl nucleus and a mantle,
    wherein the at least one selected from the group consisting of a pearl nucleus and a mantle contains a protein having 10 EU/g or less of an endotoxin amount, and
    wherein the protein having 10 EU/g or less of an endotoxin amount includes a repeating sequence of a GXY triplet, which may be separated by one or more amino acids, includes one or more RGD motifs, and has a polydispersity of less than 20.

2. The pearl culture material according to claim 1, wherein a coating amount of the protein in a surface area of the pearl nucleus or the mantle is 20 pg/mm² or more.

3. The pearl culture material according to claim 1, wherein the endotoxin amount is 2.5 EU/g or less.

4. The pearl culture material according to claim 1, wherein the protein contains at least a part of an amino acid sequence of collagen.

5. The pearl culture material according to claim 4, wherein the amino acid sequence of the collagen is an amino acid sequence of type I collagen α1 chain.

6. The pearl culture material according to claim 1, wherein the protein has a weight-average molecular weight of 30 kDa to 200 kDa, which is determined by gel permeation chromatography.

7. The pearl culture material according to claim 1, wherein the protein includes a protein derived from a genetically recombinant yeast.

8. A method of inserting a pearl nucleus into a pearl sag of a mother pearl oyster from which a pearl has been taken out, using the pearl culture material according to claim 1.

9. A method of producing a pearl using a mother pearl oyster which is subjected to nucleus insertion by the method according to claim 8.

\* \* \* \* \*